(12) United States Patent
Weimann et al.

(10) Patent No.: US 6,842,641 B2
(45) Date of Patent: ***Jan. 11, 2005

(54) METHOD AND APPARATUS FOR IN-VIVO TRANSDERMAL AND/OR INTRADERMAL DELIVERY OF DRUGS BY SONOPORATION

(75) Inventors: Ludwig Weimann, Burlington, VT (US); Richard Childs, Franklin, VT (US)

(73) Assignee: Ultra-Sonic Technologies, L.L.C., St. Albans, VT (US)

( * ) Notice: Subject to any disclaimer, the term of this patent is extended or adjusted under 35 U.S.C. 154(b) by 92 days.

This patent is subject to a terminal disclaimer.

(21) Appl. No.: 10/303,283

(22) Filed: Nov. 25, 2002

(65) Prior Publication Data

US 2003/0078533 A1 Apr. 24, 2003

Related U.S. Application Data

(63) Continuation of application No. 09/690,604, filed on Oct. 17, 2000, now Pat. No. 6,487,447.

(51) Int. Cl.[7] .............................. A61N 1/30; A61B 17/20
(52) U.S. Cl. ........................................... 604/20; 604/22
(58) Field of Search .......................... 604/20, 22; 609/9

(56) References Cited

U.S. PATENT DOCUMENTS

| | | | |
|---|---|---|---|
| 4,767,402 A | 8/1988 | Kost et al. | |
| 4,787,888 A | 11/1988 | Fox | |
| 4,821,740 A | 4/1989 | Tachibana et al. | |
| 4,893,624 A | 1/1990 | Lele | |
| 5,171,215 A | 12/1992 | Flanagan | |
| 5,295,484 A | 3/1994 | Marcus et al. | |
| 5,323,769 A | 6/1994 | Bommannan et al. | |
| 5,362,309 A | 11/1994 | Carter | |
| 5,405,614 A | 4/1995 | D'Angelo et al. | |

(List continued on next page.)

FOREIGN PATENT DOCUMENTS

| | | |
|---|---|---|
| WO | WO 97/34656 | 9/1997 |
| WO | WO 99/39763 | 8/1999 |
| WO | WO 99/66980 | 12/1999 |

*Primary Examiner*—Edward K. Look
*Assistant Examiner*—Michael Leslie
(74) *Attorney, Agent, or Firm*—Gerry J. Elman; Elman Technology Law, P.C.

(57) ABSTRACT

An apparatus for performing in-vivo sonoporation of a skin area and transdermal and/or intradermal delivery of a drug solution includes a container having an end adjacent the skin area and containing the drug solution. The container further includes an ultrasound horn having a tip submerged in the drug solution for applying ultrasound radiation to the drug solution. The ultrasound radiation has a frequency in the range of 15 KHz and 1 MHz and is applied at an intensity, for a period of time and at a distance from said skin area effective to generate cavitation bubbles. The cavitation bubbles collapse and transfer their energy into the skin area, thus causing the formation of pores in the skin area. The ultrasound radiation intensity and distance from the skin area are also effective in generating ultrasonic jets, which ultrasonic jets then drive the drug solution through the end adjacent the skin area and the formed pores into the skin.

42 Claims, 10 Drawing Sheets

U.S. PATENT DOCUMENTS

| | | |
|---|---|---|
| 5,421,816 A | 6/1995 | Lipkovker |
| 5,445,611 A | 8/1995 | Eppstein et al. ............ 604/290 |
| 5,458,140 A | 10/1995 | Eppstein et al. ............ 600/573 |
| 5,474,531 A | 12/1995 | Carter |
| 5,618,275 A | 4/1997 | Bock |
| 5,655,539 A | 8/1997 | Wang et al. |
| 5,656,016 A | 8/1997 | Ogden |
| 5,693,016 A | 12/1997 | Gumaste et al. |
| 5,770,801 A | 6/1998 | Wang et al. |
| 5,840,062 A | 11/1998 | Gumaste et al. |
| 5,885,211 A | 3/1999 | Eppstein et al. |
| 5,906,580 A | 5/1999 | Kline-Schoder et al. |
| 5,947,921 A | 9/1999 | Johnson et al. |
| 6,024,717 A | 2/2000 | Ball et al. |
| 6,030,374 A | 2/2000 | McDaniel |
| 6,041,253 A | 3/2000 | Kost et al. .................... 604/20 |
| 6,113,558 A | 9/2000 | Rosenschein et al. |
| 6,113,559 A | 9/2000 | Klopotek |
| 6,165,440 A | 12/2000 | Esenaliev |
| 6,487,447 B1 * | 11/2002 | Weimann et al. ............. 604/20 |
| 6,712,805 B2 * | 3/2004 | Weimann .................... 604/22 |

* cited by examiner

METHOD AND APPARATUS FOR IN-VIVO TRANSDERMAL AND/OR INTRADERMAL DELIVERY OF DRUGS BY SONOPORATION

CROSS-REFERENCE TO RELATED APPLICATION

This application is a continuation of U.S. patent application Ser. No. 09/690,604, filed Oct. 17, 2000, scheduled to issue Nov. 26, 2002, as U.S Pat. No. 6,487,447, the entire disclosure of which is incorporated herein by reference.

FIELD OF THE INVENTION

The present invention relates to a method and an apparatus for transdermal and/or intradermal delivery of drugs by sonoporation and more particularly to in-vivo transdermal and/or intradermal delivery of drugs.

BACKGROUND OF THE INVENTION

Transdermal and/or intradermal delivery of drugs offer several advantages over conventional delivery methods including oral and injection methods. It delivers a predetermined drug dose to a localized area with a controlled steady rate and uniform distribution, is non-invasive, convenient and painless.

Transdermal and/or intradermal delivery of drugs require transport of the drug molecules through the stratum corneum, i.e., the outermost layer of the skin. The stratum corneum (SC) provides a formidable chemical barrier to any chemical entering the body and only small molecules having a molecular weight of less than 500 Da (Daltons) can passively diffuse through the skin at rates resulting in therapeutic effects. A Dalton is defined as a unit of mass equal to $\frac{1}{12}$ the mass of a carbon-12 atom, according to "Steadman's Electronic Medical Dictionary" published by Williams and Wilkins (1996).

In co-pending patent application entitled "Method of forming micropores in skin", incorporated herein by reference, sonoporation has been proposed as a method to facilitate transdermal and/or intradermal delivery of molecules larger than 500 Da and to increase the rate of drug delivery through the SC. The sonoporation apparatus described in the referenced application is not practical for in-vivo drug delivery and in particular for treating humans.

It would be advantageous to provide a method and an apparatus for in-vivo transdermal and/or intradermal delivery of any size drug molecules.

SUMMARY OF THE INVENTION

In general, in one aspect, the invention provides an apparatus for performing in-vivo sonoporation of a skin area and transdermal and/or intradermal delivery of a drug solution including a container having an end covered with a porous membrane and containing the drug solution and an ultrasound horn having a tip submerged in the drug solution. The ultrasound horn applies ultrasound radiation to the drug solution. The ultrasound radiation has a frequency in the range of 15 KHz and 1 MHz and is applied at an intensity, for a period of time and at a distance from said skin area effective to generate cavitation bubbles. The cavitation bubbles collapse and transfer their energy into the skin area thus causing the formation of pores in the skin area. The ultrasound radiation intensity and distance from the skin area are also effective in generating ultrasonic jets, which ultrasonic jets then drive the drug solution through the porous membrane and the formed pores into the skin area.

Implementations of the invention may include one or more of the following features. The membrane may have pores with a diameter of 100 micrometers. The membrane may be hydrophobic. The tip may be removable connected to the ultrasound horn and it may have a distal end surface, which is flat or concave. The distal end surface may have a plurality of depressions. The tip may also have a body having markings indicating the amount of the drug solution contained in the container. A removable protective film may cover the membrane. The container may have an outer wall, an inner wall and an absorbent wick placed between the inner and outer wall. The wick absorbs any excess drug solution that is not driven into the skin area through the formed pores and it may be made of highly absorbent and hydrophilic material such as absorbent cellulose material, polyvinyl alcohol sponge, Sodium Carboxy-Methyl Cellulose (CMC), blotting paper and any other spongy materials.

The container inner wall may have first and second grooves and tip may have a body having first and second grooves. The tip is inserted into the container and placed so that the first and second grooves of the tip body are opposite the first and second grooves of the container inner wall. This arrangement defines first and second spaces for accommodating first and second o-rings, respectively. The container may also have an inlet septum for filling it with the solution. The container may be a cylinder made of a transparent material and/or plastic material.

The ultrasound frequency may be 20 KHz and the ultrasound intensity may be in the range of 5 W/cm$^2$ and 55 W/cm$^2$. The tip may have a distal end located at a distance from the membrane in the range of 1 millimeter to 10 millimeters. The ultrasound radiation may be continuous or pulsed and it may be applied for a period of time in the range of about 30 seconds to 5 minutes, preferably 1 minute for continuous exposure or about 10 minutes to 20 minutes for pulsed exposure with a 5% duty cycle, respectively. The formed pores may have a diameter in the range of 1 micrometer to 100 micrometers.

In general, in another aspect, the invention features a method of performing in-vivo sonoporation of a skin area and transdermal and/or intradermal delivery of a drug solution. The method includes providing a container containing a predetermined amount of the drug solution and having a first end and a second end, the second end being covered with a porous membrane. Next a tip of an ultrasound horn is submerged in the drug solution through the first end of the container and then the porous membrane is placed in contact with the skin area. The ultrasound radiation is then turned on having a frequency in the range of 15 KHz and 1 MHz. The ultrasound radiation is applied with an intensity, for a period of time and at a distance from the skin area effective to generate cavitation bubbles. The cavitation bubbles collapse and transfer their energy into the skin area thus causing the formation of pores in the skin area. The ultrasound radiation intensity and distance from the skin area are also effective in generating ultrasonic jets, which ultrasonic jets then drive the drug solution through the porous membrane and the formed pores into the skin area.

Among the advantages of this invention may be one or more of the following. The apparatus allows a painless and rapid delivery of drugs through the skin for either topical or systemic therapy. The apparatus allows coupling of the ultrasound radiation to a container containing the drug solution without dampening the ultrasound intensity.

The details of one or more embodiments of the invention are set forth in the accompanying drawings and description

BRIEF DESCRIPTION OF THE DRAWINGS

Like reference numbers and designations in the various drawings indicate like elements.

DETAILED DESCRIPTION OF THE PREFERRED EMBODIMENT

Figure 1:
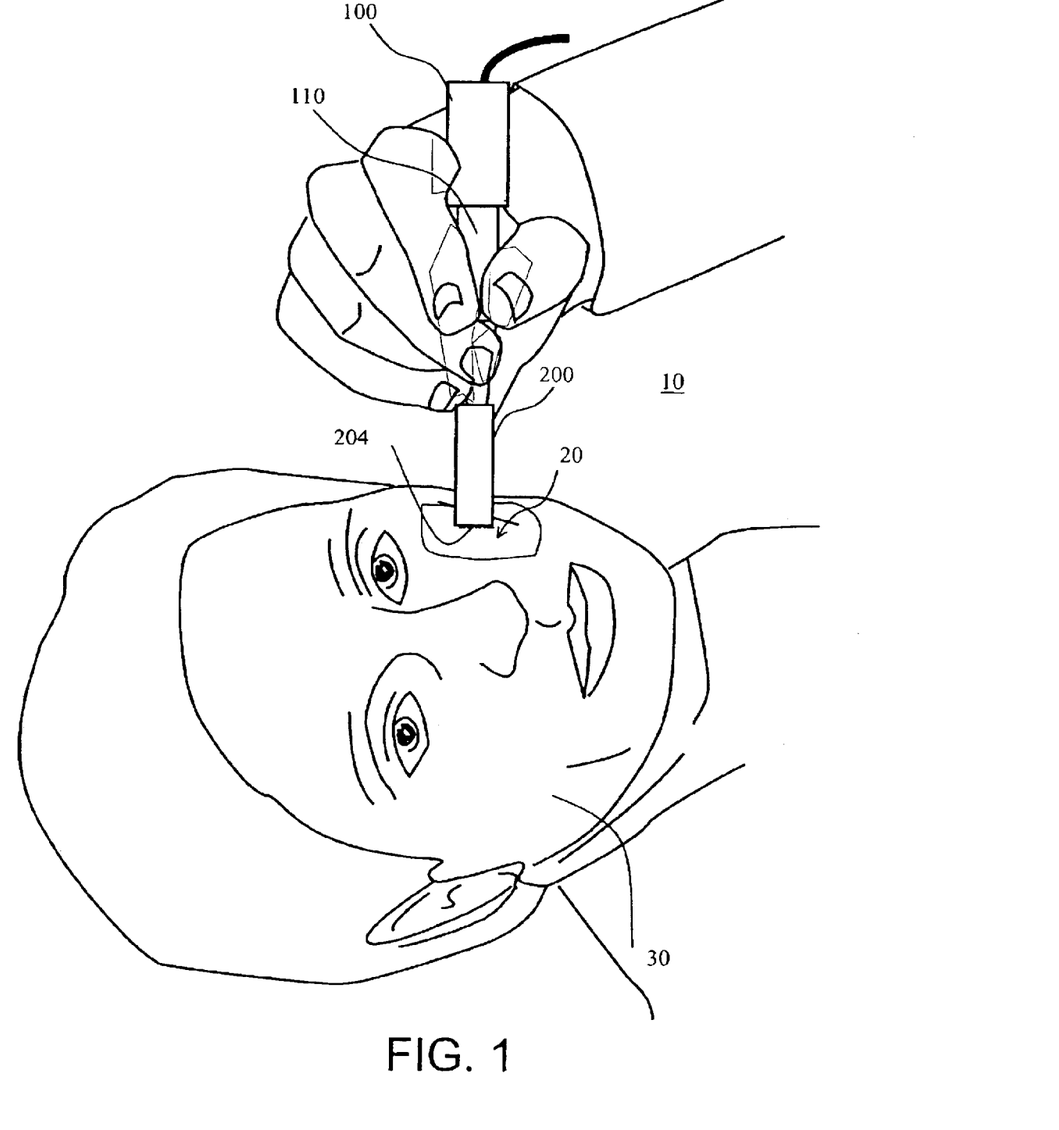
FIG. 1 is a schematic representation of in-vivo transdermal and/or intradermal delivery of an anti-inflammatory drug via an ultrasonic apparatus.

Referring to FIG. 1, an ultrasonic transdermal and/or intradermal drug delivery apparatus 10 is used to deliver an anti-inflammatory drug to a skin area 20 of a patient's face 30, which is affected with acne. The ultrasonic drug delivery apparatus 10 includes an applicator 200 that contains the liquid based anti-inflammatory drug and an ultrasonic transducer 100. Ultrasonic transducer 100 generates ultrasound waves, which then couple to the applicator 200 and ultimately to the patient's face 30 through an ultrasonic horn 110. During the treatment, the bottom surface 204 of the ultrasonic drug delivery applicator 200 is placed in contact with the affected skin area 20 and the ultrasound transducer 100 is turned on for a predetermined time period. The generated ultrasound waves have a predetermined frequency, power and duty cycle. The ultrasound waves cause sonoporation of the skin, as described in the co-pending application entitled "Method of forming micropores in skin" incorporated herein by reference. Sonoporation generates micro-pores in the skin area 20 and a predetermined amount of the anti-inflammatory drug solution is painlessly transported through the micro-pores inside the skin. This procedure is repeated as many times as necessary to cover the total affected skin area and to deliver the total prescribed amount of the anti-inflammatory drug.

Figure 2:
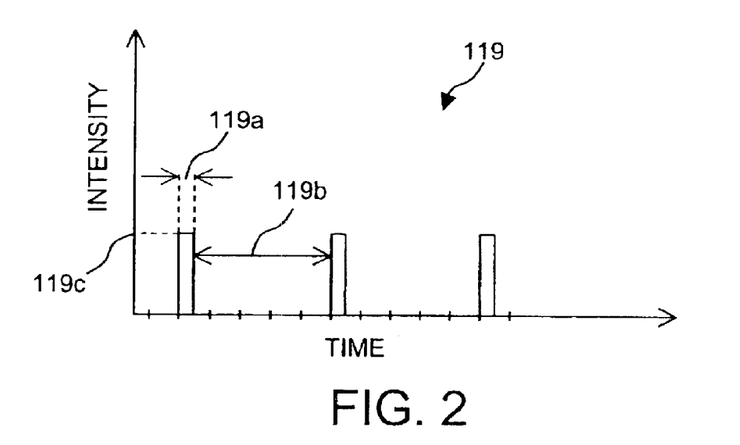
FIG. 2 is a graph depicting a pulsed ultrasound wave.

Referring to FIG. 2, in one example, the ultrasound waves are pulses 119 having a frequency of 20 KHz and intensity $119c$ of 20 W/cm$^2$. The pulse width $119a$ is 0.5 seconds, the time interval $119b$ between the end of one pulse and the beginning of the next is 9.5 seconds and the period of the ultrasound wave is 10 seconds. In one example, the skin is exposed to ultrasound for 20 minutes with a 5% duty cycle (i.e., 120 pulses with each pulse providing ultrasound energy for 0.5 seconds) resulting in a total of 1 minute of continuous ultrasound exposure.

Figure 3:
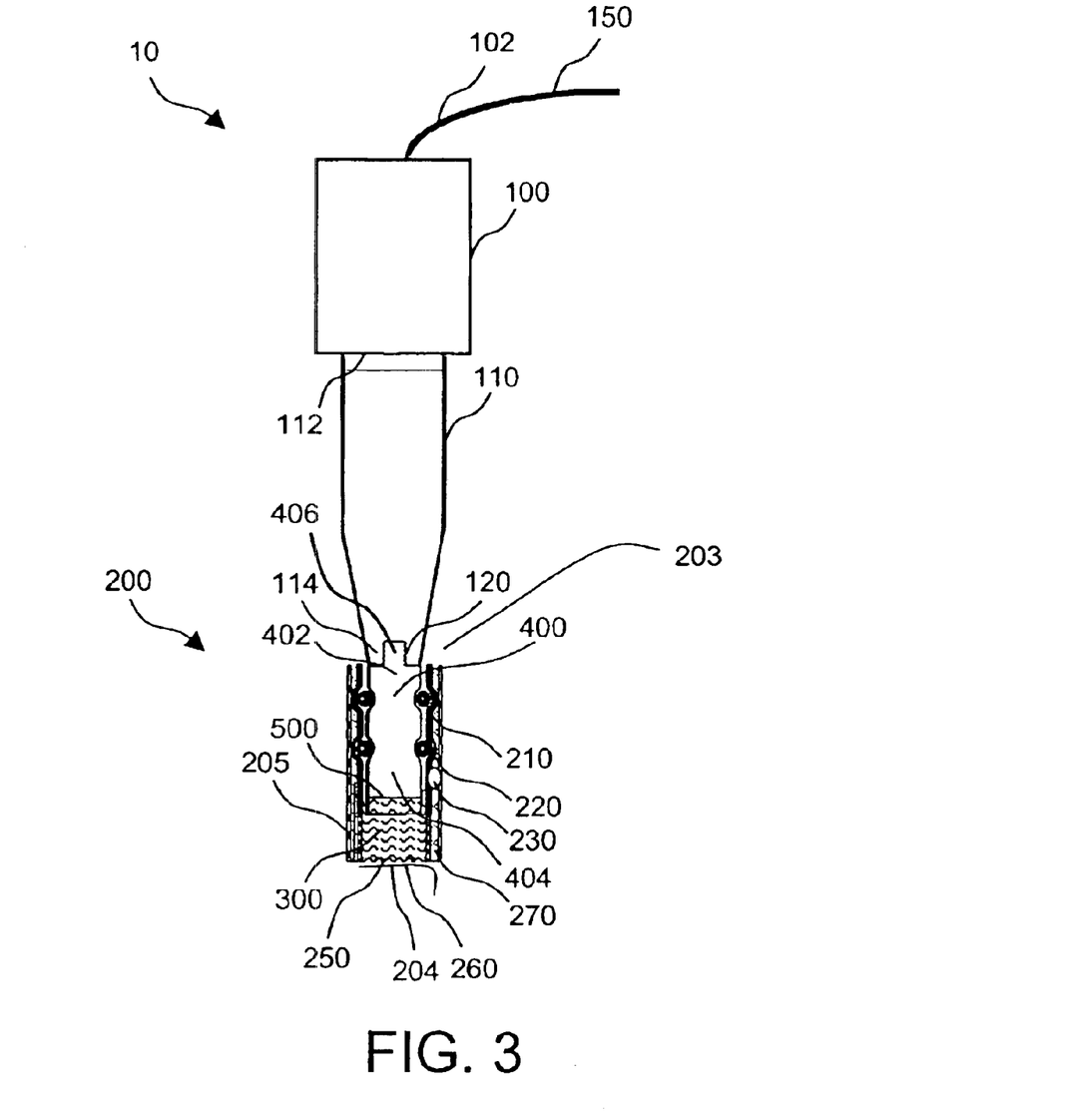
FIG. 3 is a cross-sectional side view of an ultrasonic drug delivery apparatus.

Referring to FIG. 3, ultrasonic horn 110 has a first end 112 connected to the ultrasonic transducer 100 and a second end 114 attached to a removable cylindrical tip 400. Ultrasonic transducer 100 connects via a cable 102 to a power supply 150 that energizes the transducer 100. The cylindrical tip 400 has a first end 402 with a threaded post 406 and a second end 404. Threaded post 406 is screwed into threaded hole 120 located at the second end 114 of the ultrasonic horn 110. Second end 404 of the cylindrical tip 400 has markings 500 indicating the level of the drug solution 300 contained in the applicator 200. Applicator 200 includes a cylindrical container 205 with a first open end 203 and a second end 204. Second end 204 is covered with a porous membrane 250. Membrane 250 has pores 252 with a diameter of a few micrometers, a hydrophobic, non-wettable inside surface 251 and an outside surface 254, shown in FIG. 7A. Outside surface 254 is covered with a removable protective film 260 that keeps the drug solution 300 contained in the cylindrical applicator container 200. The ultrasonic horn tip 400 is inserted into the applicator container 200 through the first open end 203. First and second O-rings, 210 and 220, respectively, keep the ultrasonic horn tip 400 submerged in the drug solution 300 and prevent leakage of the drug solution 300.

Figure 4:
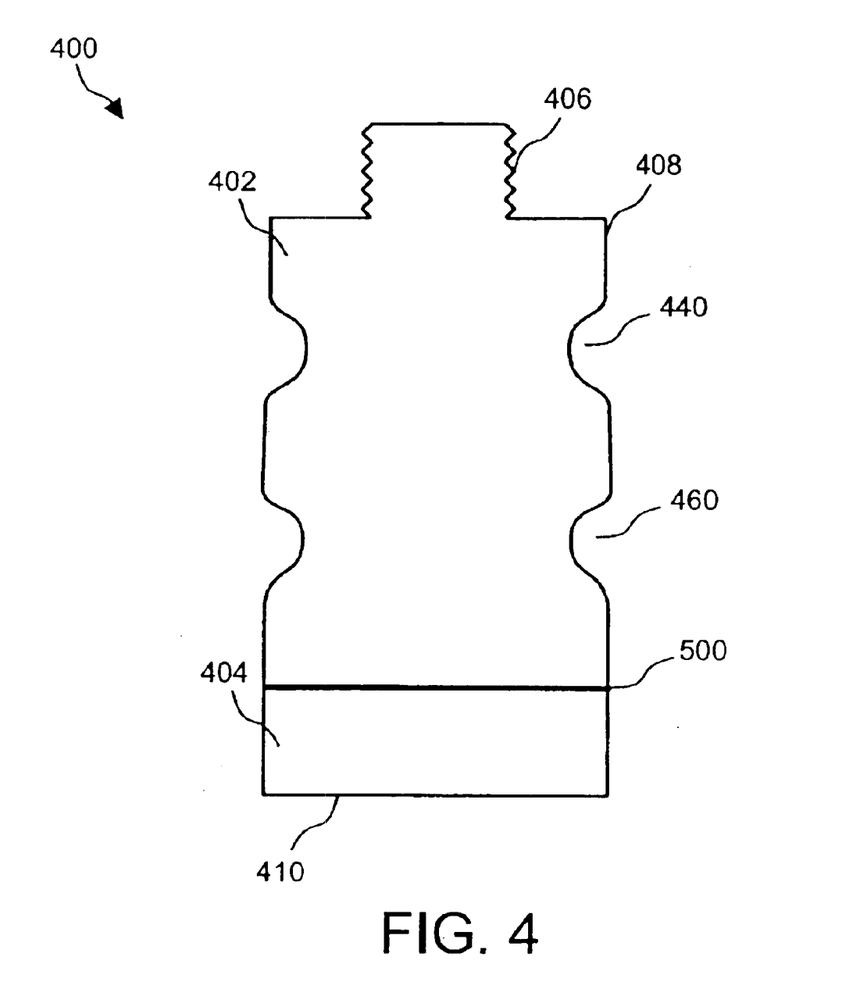
FIG. 4 is a side view of an ultrasonic horn tip with a flat surface tip area.

Referring to FIG. 4, the tip 400 of the ultrasonic horn 110 includes in addition to the above mentioned threaded post 406 and markings 500, a first groove 440 and a second groove 460 that accommodate first and second O-rings 210 and 220, respectively. In one example, the tip 400 is made of titanium and has a length of 10 cm, and a diameter of 1 cm. The bottom surface 410 of the tip 400 is flat and during the time the transducer 100 is on it emits scattered ultrasound waves that cause random micro-poration of the skin.

Figure 5:
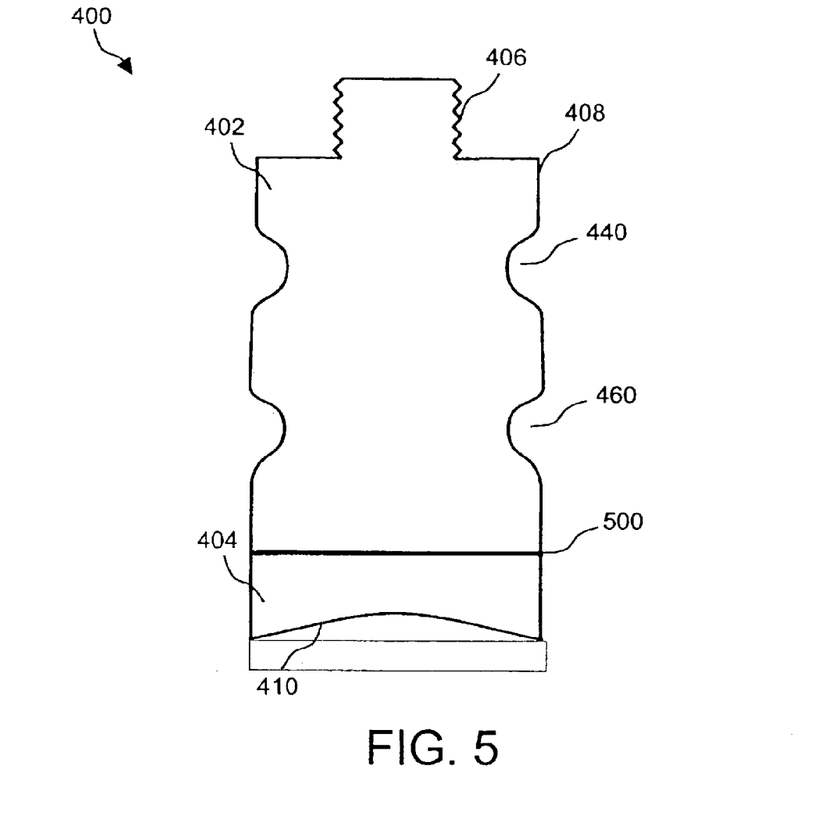
FIG. 5 is a side view of an ultrasonic horn tip with a concave surface tip area

In other embodiments the emitted ultrasound waves are focused or parallel. Referring to FIG. 5, an ultrasonic horn tip 400 with a concave bottom surface 410 is used to generate ultrasound waves that focus over a very small skin area. Focused ultrasound waves are used for deep skin micro-poration over a small skin area.

Figure 6A:
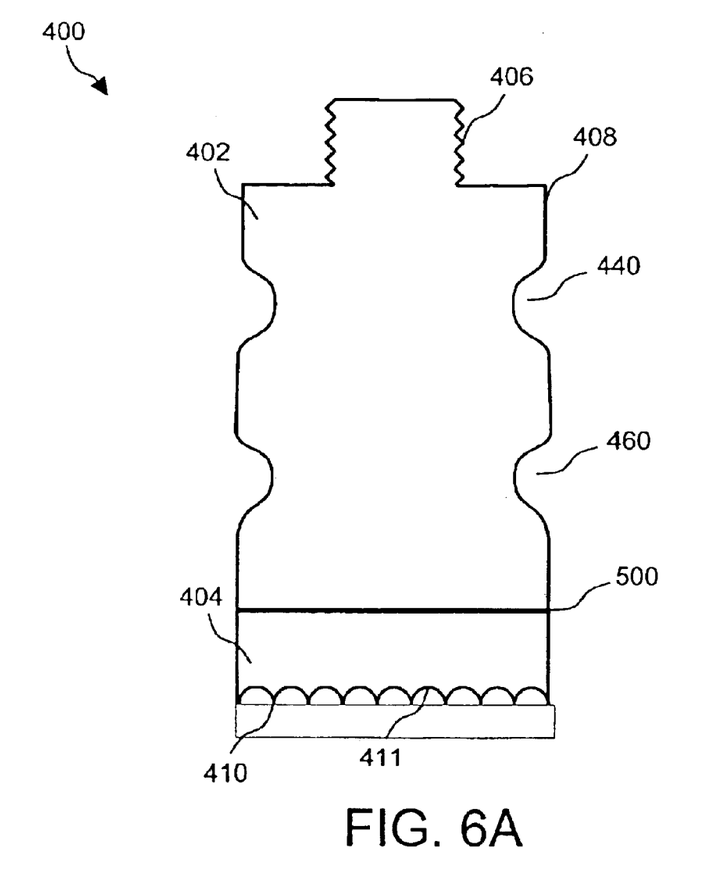
FIG. 6A side view of an ultrasonic horn tip with a tip surface having depressions.
Figure 6B:
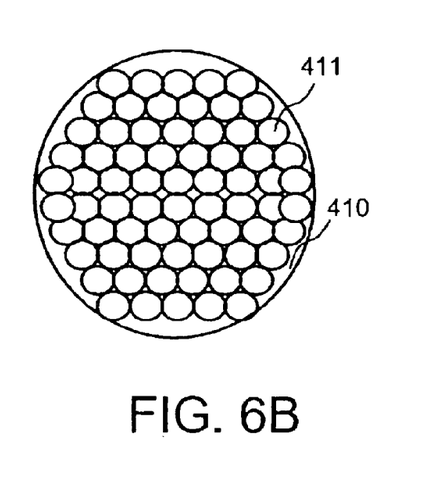
FIG. 6B is bottom view of the tip surface of FIG. 6A having depressions.

Referring to FIGS. 6A and 6B, an ultrasonic horn tip 400 with a bottom surface 410 having concave depressions 411 is used to generate parallel ultrasound waves. The overall form and direction of the ultrasound waves depends upon the shape, curvature radius, density and distribution of the depressions 411 across the bottom surface 410. In the embodiment of FIG. 6B, depressions 411 have the same shape and curvature radius and are uniformly distributed across the bottom surface 410. In alternative embodiments, the shape, curvature radius, density and distribution of the depressions are varied across the bottom surface 410. Parallel ultrasound waves are used to generate uniform distribution of micro-pores on the skin surface.

Figure 7:
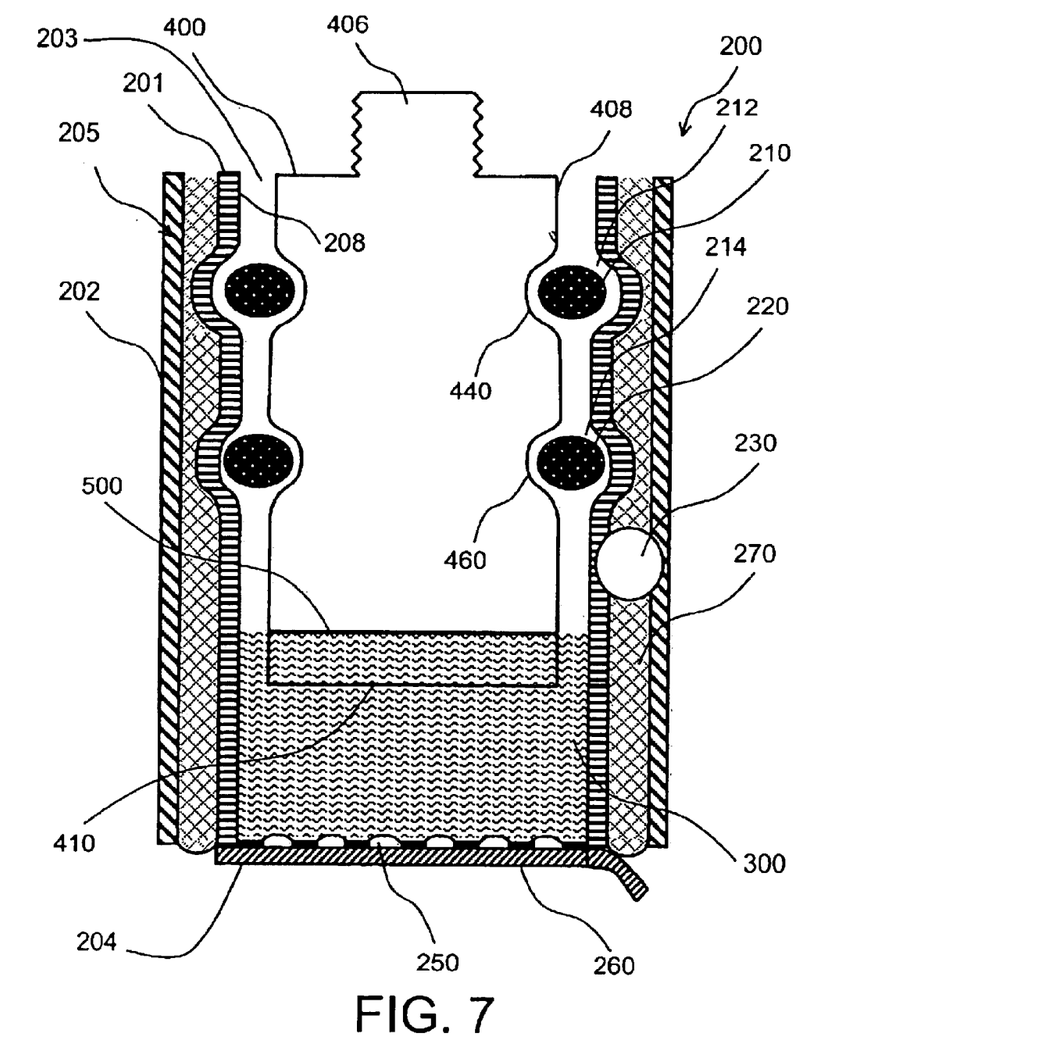
FIG. 7 is a cross-sectional side view of an ultrasonic drug delivery applicator.
Figure 7A:
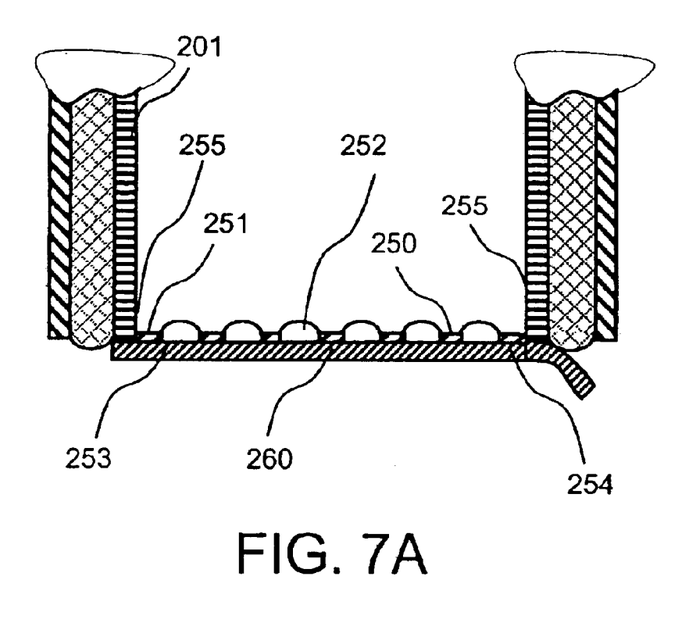
FIG. 7A is a cross-sectional side view of the porous hydrophobic membrane 250.
Figure 8:
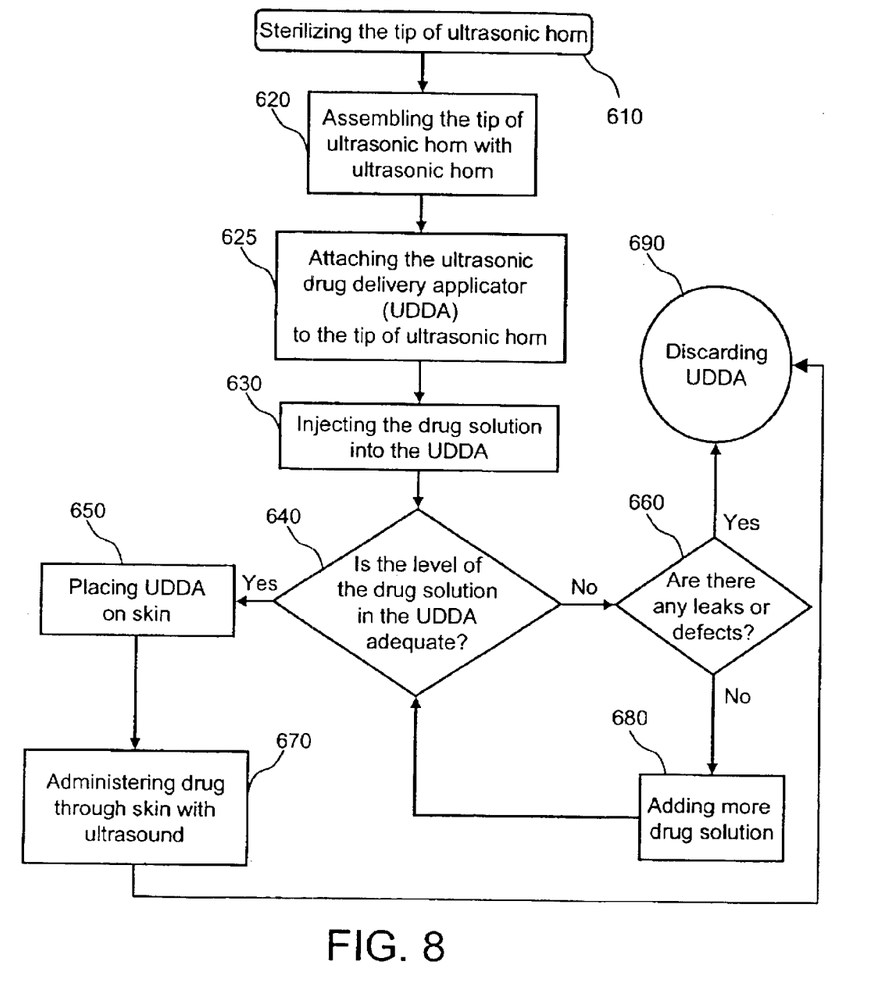
FIG. 8 is a flow diagram of an in-vivo transdermal and/or intradermal drug delivery method.

Referring to FIG. 7, a drug delivery applicator 200 includes a cylindrically shaped hollow container 205 that has an inner wall 201 spaced apart from an outer wall 202 and a wick 270 situated in the space between inner wall 201 and outer wall 202. The container 205 is preferably made of a transparent hard plastic material and is discarded after use. The wick 270 is made of a highly absorbent and hydrophilic material. In one example, the wick 270 is made of a high-absorbency polyvinyl alcohol sponge (PVA), manufactured by the M-Pact company under the tradename of CLINICEL™. Other examples of highly absorbent and hydrophilic material include HYDROFERA™ PVA sponge manufactured by Hydrofera LLC, Sodium Carboxy-Methyl Cellulose (CMC), blotting paper and any other spongy material. Both the inner and outer applicator walls 201, 202 are basically cylindrical and axially aligned, with the exception of two locations on the inner surface 208 of the inner applicator wall 201 where two grooves 212 and 214 are cut out. Grooves 212 and 214 are aligned and placed opposite grooves 440 and 460 cut into the outer surface 408 of the ultrasonic horn tip 400, respectively. O-rings 210 and 220 occupy the space formed between the oppositely placed grooves 212, 440 and 214, 460, respectively. O-rings 210 and 220 facilitate a secure and leak proof fit of the ultrasonic horn tip 400 into the drug delivery applicator 200.

Again with reference to FIG. 7, the drug solution inlet septum 230 is located between the outer applicator wall 202 and the inner applicator wall 201 approximately halfway between the open top 203 and bottom surface 204 of the ultrasonic drug delivery applicator 200. The septum 230 is constructed of a silicon rubber material, designed to be impervious to liquids yet allow injection of the drug solution into the ultrasonic drug delivery applicator 200 using a hypodermic needle.

Referring to FIG. 7A, porous membrane 250 is attached to the bottom 255 of the inner applicator container wall 201. Membrane 250 is constructed of a hydrophobic material that resists the passage of the aqueous liquid due to its non-wettable inner surface 251 and has pores 252 with a diameter in range of 10 to 100 micrometers, preferably with diameter of 50 micrometers. In one example, membrane 250 is made of a non-woven polypropylene. The bottom surface 253 of membrane 250 is covered with a removable protective film 260. In one example, the removable protective film 260 is a thin plastic sheet that is attached to the membrane via a silicon based adhesive 254.

In operation, a sterilized ultrasonic drug delivery applicator 200 is placed over the tip of ultrasonic horn 400. A predetermined drug solution 300 is then introduced into the cylindrical applicator container 205 through the inlet septum 230 via a hypodermic needle (not shown). When the ultrasonic drug delivery applicator 200 is properly filled, the tip of the ultrasonic horn 400 is partially immersed in the solution 300. Visual inspection of the solution level marking 500 indicates whether the applicator is properly filled, and whether the ultrasonic drug delivery applicator 200 is leaking or defective. Once the ultrasonic drug delivery applicator 200 is filled and determined to be ready for use, the protective film 260 is peeled-off exposing the porous membrane 250. The apparatus 10 is then placed on the patient's skin, oriented such that the porous membrane 250 is flush with the skin area where the drugs are to be administered and such that the bottom of the horn tip 410 is immersed in drug solution 300. A timer (not shown), which is included in the power supply, is set to a pre-determined length of time for sonoporation. The power supply is switched on, and the apparatus sonoporates the skin for an allotted amount of time.

The membrane 250 resists passage of the aqueous drug solution 300 due to its non-wettable inside surface 251 and the small size diameter pores. A quantity called the breakthrough pressure (P) is used to quantify the hydraulic pressure of the liquid drug that is needed to break through the porous membrane. The breakthrough pressure (P) is described by the following mathematical formula:

$$P=(-4\gamma \cos \zeta)/D \qquad \text{Equation 1}$$

Where:

$\gamma$ is the surface tension of the liquid, $\zeta$ is the contact angle formed between the liquid and the smooth surface of the membrane, D is the effective pore diameter of the membrane When the pressure of the drug solution is less than $(-4\gamma \cos \zeta)/D$, the drug solution 300 remains contained inside the applicator container 205. In this case, the purpose of the porous membrane is to prevent the drug solution from leaking prior to transdermal or intradermal infusion process while allowing the ultrasound waves to freely pass through and reach the skin surface 20 and to generate the micro-pores in the stratum corneum. When the pressure of the drug solution 300 is higher than $(-4\gamma \cos \zeta)/D$, the drug solution 300 passes through the membrane pores and reaches the skin surface 20, from where it is then transported via the ultrasonic jet pressure through the skin micro-pores into the skin. Excess liquid transferred to the skin during the ultrasound exposure is absorbed by the wicking action of wick 270. After use, the ultrasonic drug delivery applicator 200 is removed form the ultrasound tip and discarded.

Referring to FIG. 8, a method 600 of transdermal and/or intradermal drug delivery using the drug delivery applicator of the present invention includes the general steps of preparing the sonoporation apparatus for use, verifying that it is functioning normally, exposing a patient's skin to ultrasound and administering drugs.

In particular, in the preparation step, an operator first sterilizes 610 the tip of the ultrasonic horn, then assembles 620 the ultrasonic horn tip with the ultrasonic horn, then attaches 625 the ultrasonic drug delivery applicator (UDDA) to the ultrasonic horn tip and finally injects 630 the drug solution into the UDDA.

The ultrasonic horn tip 400 may be sterilized using an ethylene oxide gas or by exposing the horn tip 400 to steam. The horn tip may also be pre-sterilized and sealed in a protective package. The sterilized ultrasonic horn tip 400 is attached to the ultrasonic horn 110 by screwing the threaded post 406 of the tip 400 into the threaded hole 120 of the ultrasonic horn 110. The UDDA is attached to the tip of the ultrasonic horn 400 by inserting the device onto the tip 400, as described in FIG. 7. The drug solution 300 is injected into the ultrasonic drug delivery applicator 200 via the inlet septum 230 using a syringe.

In the function verification step 640 the operator compares the level of the drug solution 300 in the ultrasonic drug delivery applicator 200 to the level marking 500 via a visual inspection. If the levels are aligned the operator proceeds with the treatment by first removing the protective film 260 from the ultrasonic drug delivery applicator 200, then orienting and placing 650 the apparatus on the patient's skin so that the porous membrane is flush with the skin surface and the tip of the ultrasonic horn 400 is immersed in the drug solution 300.

Next the operator administers 670 the drug solution. For this purpose, the ultrasound power is turned on for a predetermined period of time, and ultrasound waves are generated having a frequency, power and duty cycle so that they cause formation of micro-pores in the skin and subsequently transfer the drug from the ultrasonic drug delivery applicator 200 through the skin micro-pores and across the SC into the blood vessels of the blood capillary system. At the end of a successful treatment the power supply is set to a stand-by condition and the UDDA is discarded 690.

If in the function verification step 640 the levels are not aligned, the operator proceeds to check 660 via a visual inspection if there are any leaks or defects in the UDDA. If there are no obvious sources of error, the operator adds 680 more drug solution to fill the UDDA to the appropriate level and then checks 640 again the levels. If the UDDA appears to be leaking or is otherwise defective, the operator discards 690 the defective UDDA and repeats step 625.

The many features and advantages of the present invention are apparent from the detailed specification, and thus, it is intended by the appended claims to cover all such features and advantages of the described apparatus that follow the true spirit and scope of the invention. Furthermore, since numerous modifications and changes will readily occur to those of skill in the art, it is not desired to limit the invention to the exact construction and operation described herein. Moreover, the process and apparatus of the present invention, like related apparatus and processes used in medical applications tend to be complex in nature and are often best practiced by empirically determining the appropriate values of the operating parameters or by conducting computer simulations to arrive at a best design for a given application. Accordingly, other embodiments are within the scope of the following claims.

What is claimed is:

1. An apparatus for performing in-vivo sonoporation of skin area and transdermal and/or intradermal delivery of a drug solution comprising: an ultrasound horn having a tip submerged in said drug solution and applying ultrasound radiation to said drug solution wherein said ultrasound radiation has a frequency in the range of 15 KHz and 1 MHz and is applied at an intensity, for a period of time and at a distance from said skin area effective to generate cavitation bubbles, wherein said cavitation bubbles collapse and transfer their energy into the skin area thus causing the formation of pores in the skin area; and wherein said ultrasound radiation intensity and distance from the skin area are also effective in generating ultrasonic jets, said ultrasonic jets driving said drug solution transdermally through said formed pores into the skin area.

2. The apparatus of 1 wherein said formed pores have a diameter in the range of 1 micrometer to 100 micrometers.

3. The apparatus of 1 wherein said tip is removably connected to said ultrasound horn.

4. The apparatus of 1 wherein said tip comprises a flat distal end surface.

5. The apparatus of 1 wherein said tip comprises a concave distal end surface.

6. The apparatus of claim 1 wherein said tip comprises a distal end surface having a plurality of depressions.

7. The apparatus of claim 1 wherein said tip comprises a body having markings indicating the amount of the drug solution contained in the container.

8. The apparatus of claim 1 further comprising a container which comprises: an outer wall; an inner wall; and an absorbent wick placed between said inner and outer wall, said wick absorbing any excess drug solution that is not driven into the skin area through the formed pores.

9. The apparatus of 8 wherein said wick comprises a spongy material having highly absorbent and hydrophilic properties.

10. The apparatus of 8 wherein said wick comprises a highly absorbent and hydrophilic material selected from the group consisting of absorbent cellulose material, polyvinyl alcohol sponge, sodium carboxy-methyl cellulose, and blotting paper.

11. The apparatus of 8 wherein said inner wall comprises first and second grooves, said tip comprises a body having first and second grooves and wherein said first and second grooves of the tip body are arranged opposite said first and second grooves of the container inner wall, the arrangement defining first and second spaces for accommodating first and second o-rings, respectively.

12. The apparatus of 8 wherein said container further comprises an inlet septum for filling said container with the solution.

13. The apparatus of claim 8 wherein said container is a cylinder.

14. The apparatus of claim 8 wherein said container comprises a transparent material.

15. The apparatus of claim 8 wherein said container comprises a plastic material.

16. The apparatus of claim 1 wherein said ultrasound frequency is 20 KHz.

17. The apparatus of claim 1 wherein said ultrasound intensity is in the range of 5 W/cm$^2$ and 55 W/cm$^2$.

18. The apparatus of claim 1 wherein said tip has a distal end located at a distance from said skin area in the range of 1 millimeter to 10 millimeters.

19. The apparatus of claim 1 wherein said ultrasound radiation is continuous.

20. The apparatus of claim 1 wherein said ultrasound radiation is pulsed.

21. The apparatus of claim 1 wherein said period of time is in the range of about 30 seconds to 5 minutes of continuous exposure to said ultrasound radiation.

22. The apparatus of claim 1 wherein said period of time is in the range of about 10 minutes to 20 minutes of pulsed exposure to said ultrasound radiation with a 5% duty cycle.

23. The apparatus of claim 1 further comprising a container having an end covered with a membrane at the skin area and containing said drug solution, wherein said membrane is hydrophobic.

24. A method of performing in-vivo sonoporation of a skin area and transdermal and/or intradermal delivery of a drug solution comprising: providing a container containing a predetermined amount of said drug solution; submerging a tip of an ultrasound horn in said drug solution through said container; placing said container in contact with said skin area; and applying ultrasound radiation to said drug solution wherein said ultrasound radiation has a frequency in the range of 15 KHz and 1 MHz and is applied at an intensity, for a period of time and at a distance from said skin area effective to generate cavitation bubbles, wherein said cavitation bubbles collapse and transfer their energy into the skin area thus causing the formation of pores in the skin area; and wherein said ultrasound radiation intensity and distance from the skin area are also effective in generating ultrasonic jets, said ultrasonic jets driving said drug solution transdermally through said formed pores into the skin area.

25. The method of claim 24 wherein said tip is removably connected to said ultrasound horn comprising before submerging said tip in said drug solution attaching said tip to said ultrasound horn.

26. The method of claim 25 further comprising sterilizing said tip before attaching it to said ultrasound horn.

27. The method of claim 24 wherein said tip comprises a flat distal end surface.

28. The method of claim 24 wherein said tip comprises a concave distal end surface.

29. The method of claim 24 wherein said tip comprises a distal end surface having a plurality of depressions.

30. The method of claim 24 wherein said tip comprises a body having markings indicating the amount of the drug solution contained in the container.

31. The method of claim 30 further comprising checking the amount of said drug solution contained in the container before applying said ultrasound radiation.

32. The method of claim 31 further comprising adding drug solution to said container.

33. The method of claim 24 wherein said container comprises: an outer wall; an inner wall; and an absorbent wick placed between said inner and outer wall, said wick absorbing any excess drug solution that is not driven into the skin area through the formed pores.

34. The method of claim 24 wherein said ultrasound frequency is 20 KHz.

35. The method of claim 24 wherein said ultrasound intensity is in the range of 5 W/cm$^2$ and 55 W/cm$^2$.

36. The method of claim 24 wherein said tip has a distal end located at a distance from said skin area in the range of 1 millimeter to 10 millimeters.

37. The method of claim 24 wherein said ultrasound radiation is continuous.

38. The method of claim 24 wherein said ultrasound radiation is pulsed.

39. The method of claim 24 wherein said period of time is in the range of about 30 seconds to 5 minutes of continuous exposure to said ultrasound radiation.

40. The method of claim 24 wherein said period of time is in the range of about 10 minutes to 20 minutes of pulsed exposure to said ultrasound radiation with a 5% duty cycle.

41. The method of claim 24 wherein said formed pores have a diameter in the range of 1 micrometer to 100 micrometers.

42. The method of claim 24 wherein, said the container comprising a hydrophobic membrane adjacent to the skin area.

* * * * *